United States Patent
Barbacid (12)

(10) Patent No.: US 6,271,242 B1
(45) Date of Patent: Aug. 7, 2001

(54) METHOD FOR TREATING CANCER USING A TYROSINE PROTEIN KINASE INHIBITOR

(75) Inventor: Mariano Barbacid, Lawrenceville, NJ (US)

(73) Assignee: Bristol-Myers Squibb Co., New York, NY (US)

(*) Notice: Subject to any disclaimer, the term of this patent is extended or adjusted under 35 U.S.C. 154(b) by 0 days.

(21) Appl. No.: 07/834,065

(22) Filed: Feb. 10, 1992

(51) Int. Cl.$^7$ ..................................................... A01N 43/40
(52) U.S. Cl. ............................................. 514/320; 514/211
(58) Field of Search ................................. 514/211, 211.08

(56) References Cited

FOREIGN PATENT DOCUMENTS

62/155284    7/1987  (JP) .

OTHER PUBLICATIONS

T. Toaka et al., Biochemical and Biophysical Research Communication, vol. 170, No. 3, pp. 1151–1156, 1990.
M. M. Berg et al., The Journal of Biological Chemistry, vol. 267, No. 1, pp. 13–16, 1992.
G. Powis et al., Clinical Biochemistry, vol. 24, pp. 385–397, 1991.
S. Akinaga et al., Cancer Chemotherapy and Pharmacology, vol. 29, No. 4, pp. 266–272, 1992.
Patent Abstracts of Japan, vol. 13, No. 442 (C–641) (3790), Oct. 4, 1989.
Elliot, L.H. et al., Biochem. Biophys. Res. Commun. 171, 148–154 (1990). "K252a is a Potent and SElective Inhibitor of Phosphorylase Kinase."
Hashimoto, S., J. Cell. Biol., 107, 1531–1539 (1988). "K–252a, a Potent Protein Kinase Inhibitor, Blocks Nerve Growth Factor–induced Neurite Outgrowth and Changes in the Phosphorylation of Proteins in PC12h Cells."
Koizumi, S. et al., J. Neurosci., 8, 715–721 (1988). "K–252a: A specific Inhibitor of the Action of Nerve Growth Factor on PC12 Cells."
Nakanishi, S. et al., J. Antibiot., 39, 1066–1071 (1986). "K–252b, .c and D, Potent Inhibitors of Protein Kinase C From Microbial Origin."

Nakanishi, S. et al., J. Biol. Chem., 263, 6215–6219 (1988). "K–252a, a Novel Microbial Product, Inhibits Smooth Muscle Myosin Light Chain Kinase."
Ruegg, U.T. and Burgess, G.M., Trends Pharmacol. Sci., 10, 218–220 (1989). "Staurosporine, K–252 and UCN–01: potent but nonspecific inhibitors of protein kinases."
Lazarovici, B. et al., J. Neurosci. Res., 23, 1–8 (1989). "K–252a Inhibits the Increase in c–fos Transcription and the Increase in Intracellular Calcium Produced by Nerve Growth Factor in PC12 Cells."
Geissler, J.F. et al., J. Biol. Chem. 265, 22255–22261, (1990). "Thiazolidine–Diones."
Meyer, T. et al., INt. J. Cnacer 43, 851–856 (1989). "A derivative of Staurosporine (CGP 41 251) Shows Selectivity For Protein Kinase C Inhibition and In Vitro Anti–Proliferative as Well as In Vivo Anti–Tumor Activity."
Kase, H. et al., Biochem. and Biophys. Res. Comm. 142, 436–440 (1987). "K–252 Compounds, Novel and Potent Inhibitors of Protein Kinase C and Cyclic Nucleotide–Dependent Protein Kinases."
Fujita–Yamaguchi, Y. and Satish, K., Biochem. and Biophys. Res. Comm., 157, 955–962 (1988). "Characterization of Recepotr Tyrosine–Specific Protein Kinases By The Use of Inhibitors. Staurosporine Is A 100–Times More Potent Inhibitor of Insulin Receptor Than IGF–1 Receptor."
Nakano, H. et al., J. of Antibiotics 5, 706–708 (1987). "Staurosporine Inhibits Tyrosine–Specific Protein Kinase Activity of Rous Sarcoma Virus Transforming Protein p60."
Kase, H. et al., J. of Antibiotics 8, 1059–1065 (1986). "K–252a, A Potent Inhibitor of Protein Kinase C From Microbial Origin."
Tomaoki, T. et al., Biochem. and Biophys. Res. Comm. 135, 397–402 (1986). "Staurosporine, A Potent Inhibitor of Phospholipid/CA++Dependent Protein Kianse."

*Primary Examiner*—Jerome D. Goldberg
(74) *Attorney, Agent, or Firm*—Christopher A. Klein; Timothy J. Gaul

(57) ABSTRACT

A novel method for preventing, stabilizing or causing regression of cancer is disclosed. The method comprises administering to a patient in need thereof a tyrosine protein kinase inhibitor.

3 Claims, 8 Drawing Sheets

US 6,271,242 B1

METHOD FOR TREATING CANCER USING A TYROSINE PROTEIN KINASE INHIBITOR

BACKGROUND OF THE INVENTION

It is presently known that many human diseases are caused at least in part by proteins present in the cells of the afflicted individual. For example, certain proteins encoded by oncogenes are known to be responsible for the production of cancer in humans.

Included among these oncogenes is the oncogene designated as trk. The trk locus was originally identified by virtue of its activation as an oncogene in various human tumors (Martin-Zanca, D., et al. (1986). *Nature*, 319, 743–748). Subsequent studies revealed that the corresponding normal gene, the trk proto-oncogene, encodes a 790 amino acid-long cell surface receptor with intrinsic tyrosine protein kinase activity [(Martin-Zanca, D., et al. (1989). *Mol. Cell. Biol.*, 9, 24–33)]. This protein, designated gp140$^{trk}$, binds nerve growth factor (NGF) with high affinity, either by itself (Klein, R., et al. (1991). *Cell*, 65, 189–197) or in combination with a second NGF receptor, p75$^{LNGFR}$ (Hempstead, B. L., et al. (1991), *Nature*, 350, 678–683). Accumulative evidence indicates that gp140$^{trk}$ mediates the functional activity of NGF. NGF induces the rapid autophosphorylation of gp140$^{trk}$ on tyrosine residues, a step necessary to activate the receptor and to initiate the flow of signal transduction (Kaplan, D. R., et al. (1991). *Nature*, 350, 158–160; Kaplan, D. R., et al. (1991). *Science*, 252, 554–558; Klein, R., et al. (1991). *Cell*, 65, 189–197). Moreover, addition of NGF to NIH3T3 cells ectopically expressing gp140$^{trk}$ receptors induces the transient expression of c-Fos protein, DNA synthesis and morphologic transformation (Cordon-Cardo, C., et al. (1991). *Cell*, 66, 173–183). Similarly, addition of NGF to Xenopus oocytes microinjected with trk proto-oncogene mRNA induces germinal vesicle breakdown (Nebreda, A. R., et al. (1991). *Science*, 252, 558–561). Finally, transfection of NGF-unresponsive PC12 cells with a trk cDNA clone restores the ability of these mutant cells to respond to NGF (Loeb, D. M., et al. (1991). *Cell*, 66, 961–966).

Neoplasia is a process by which the controlling mechanisms that regulate cell growth and differentiation are impaired, resulting in progressive growth. During neoplasia, there is a characteristic failure to control cell turnover and growth. This lack of control causes a tumor to grow progressively, enlarging and occupying space in vital areas of the body. If the tumor invades surrounding tissue and is transported to distant sites, death of the individual often results.

The preferential killing of cancer cells while minimizing deleterious effects on normal cells is the desired goal in cancer therapy. In the past this has been accomplished using a variety of procedures. These procedures include the administration of chemicals (chemotherapy), radiation (radiotherapy), and surgery.

Recently there has been a rapid expansion of cancer treatments. Even though new treatments are being developed, the need still exists for improved methods for the treatment of most types of cancers.

SUMMARY OF THE INVENTION

In accordance with the present invention, a novel method for preventing, stabilizing or causing the regression of cancer caused in whole or part by a tyrosine protein kinase is disclosed. The method comprises the administration of a therapeutically effective amount of a tyrosine protein kinase inhibitor to a mammalian species in need of such treatment.

As used in the present application, the term "cancer" is used in its broadest sense and includes tumors, neoplasms, carcinomas, sarcomas, leukemias, lymphomas and the like.

As used in the present application, the term "tyrosine protein kinase inhibitor" means a substance which is able to prevent or reduce the ability of a tyrosine protein kinase enzyme to catalyze a phosphorylation reaction.

The phrase "stabilizing" cancer as used in the present application refers to slowing down the development of and/or inhibiting the formation of new cancerous lesions.

The phrase "causing the regression of" cancer as used in the present application refers to reducing and/or eliminating cancerous lesions.

DESCRIPTION OF THE FIGURES

FIG. 1. Differential effect of K252a on the neuronal differentiation of PC12 cells induced by NGF and FGF. PC12 cells were grown in collagen-coated plates for 24 hours prior to the addition of the neurotrophic factors. Cells were then incubated with either 50 ng/ml of NGF (closed circles) or 50 ng/ml of a mixture of acidic and basic FGFs (open triangles) in the absence or presence of various concentrations of K252a. Cells were visually examined for the presence of neurite outgrowth after three days. Positive neurite-bearing cells were defined as those exhibiting neurite outgrowths longer than two cell diameters. At least 500 cells were counted in each case. Values were normalized to the proportion of neurite-bearing cells induced by NGF (46% of the total cells) or FGF (29.6% of the total cells) in the respective control cultures without K252a.

Figure 2:
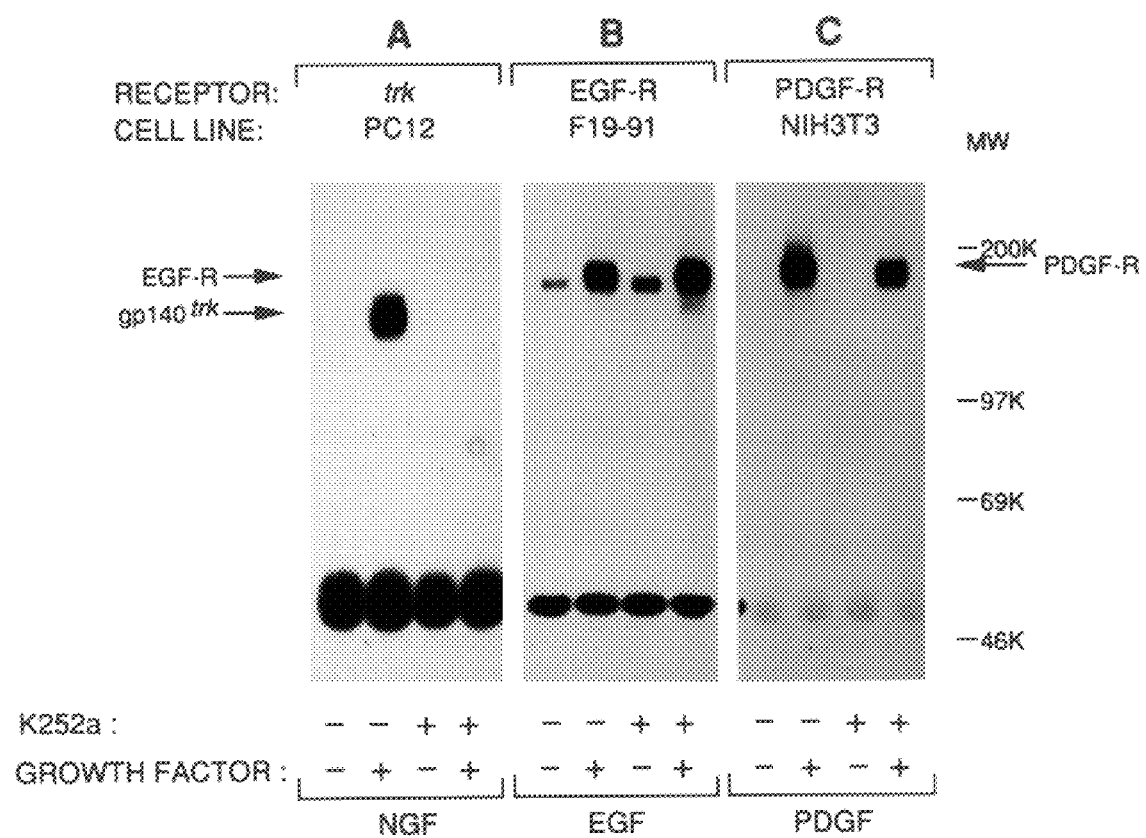
FIG. 2. K252a inhibits NGF-induced tyrosine phosphorylation of gp140$^{trk}$. (A) PC12 cells and quiescent (B) F19-91 and (C) NIH3T3 cells were incubated for 18 hours in the absence (−) or presence (+) of 100 nM K252a. Cells were then incubated for an additional 5 minutes in the absence (−) or presence (+) of 100 ng/ml of (A) NGF, (B) EGF, or (C) PDGF prior to their lysis in P-TYR buffer (see Materials and Methods herein below). Cell lysates were incubated with antisera elicited against (A) gp140$^{trk}$, (B) EGF receptor (EGF-R), or (C) PDGF receptor (PDGF-R). The resulting immunoprecipitates were analysed by 8% SDS-PAGE, transferred to nitrocellulose filters and blotted with anti-phophotyrosine monoclonal antibody 4G10. Filters were incubated with [$^{125}$I]-protein A and exposed to Kodak X-Omat film at −70° C. with the help of intensifying screens for 2 to 18 hours. The migration of gp140$^{trk}$, EGF-R and PDGF-R is indicated by arrows. Co-electrophoresed molecular weight markers included myosin (2000,000), phosphorylase b (97,000), bovine serum albumin (69,000) and ovalbumin (46,000).

SDS-PAGE, transferred to nitrocellulose filters and blotted with anti-phophotyrosine monoclonal antibody 4G10. Filters were incubated with [$^{125}$I]-protein A and exposed to Kodak X-Omat film at −70° C. with the help of intensifying screens for 30 hours. The migration of the phosphorylated gp140$^{trk}$ receptor is indicated by an arrow. The open arrow indicates the migration of gp110$^{trk}$, a phosphorylated precursor of gp140$^{trk}$ [Martin-Zanca, D., et al., Mol. Cell. Biol. 9, 24–33, (1989)]. Co-electrophoresed molecular weight markers were those described in the legend to FIG. 2.

Figure 4:
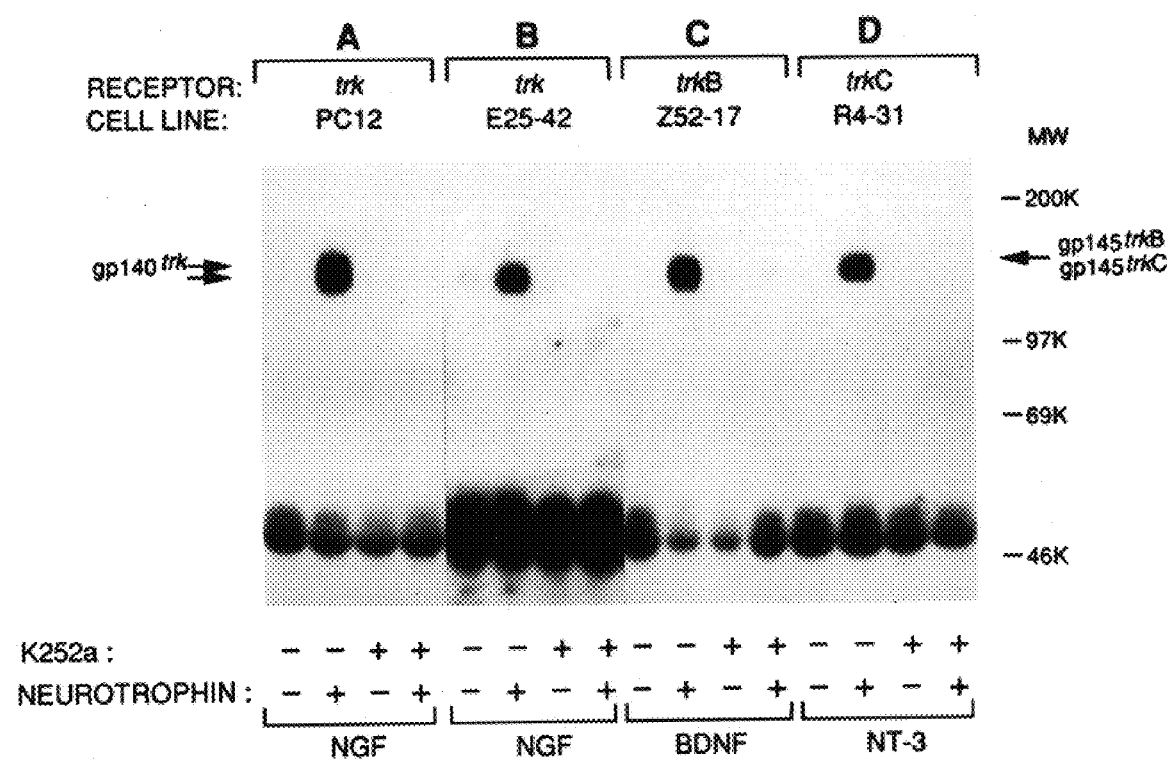

FIG. 4. K252a inhibits ligand-induced tyrosine phosphorylation of the trk family of receptors. (A) PC12 cells and quiescent (B) E25-42, (C) Z52-17 and (D) R4–31 cells were incubated for 18 hours in the absence (−) or presence (+) of 100 nM K252a. Cells were then incubated for an additional 5 minutes (PC12 cells) or 10 minutes (E25-42, Z52-17 and R4–31 cells) with (+) or without (−) 100 ng/ml of (A,B) NGF, (C) BDNF or (D) NT-3 prior to their lysis in P-TYR buffer. Cell lysates were immunoprecipitated with an anti-peptide antiserum elicited against the carboxy-terminus of gp140$^{trk}$ [(Martin-Zanca, D. et al., Mol. Cell. Biol. 9, 24–33, (1989)], which also recognizes the gp145$^{trkB}$ and gp145$^{trkC}$ receptors. The resulting immunoprecipitates were fractionated by 8% SDS-PAGE, transferred to nitrocellulose filters and blotted with anti-phosphotyrosine monoclonal antibody 4G10. Filters were incubated with [$^{125}$I]-protein A and exposed to Kodak X-Omat film at −70° C. with the help of intensifying screens for 12 to 48 hours. The migration of the gp140$^{trk}$, gp145$^{trkB}$ and gp145$^{trkC}$ tyrosine protein kinases is indicated by arrows. It should be noted that the migration of gp140$^{trk}$ in PC12 and E25–42 cells varies slightly, most likely due to differential glycosylation. Co-electrophoresed molecular weight markers were those described in the legend to FIG. 2.

Figure 5:
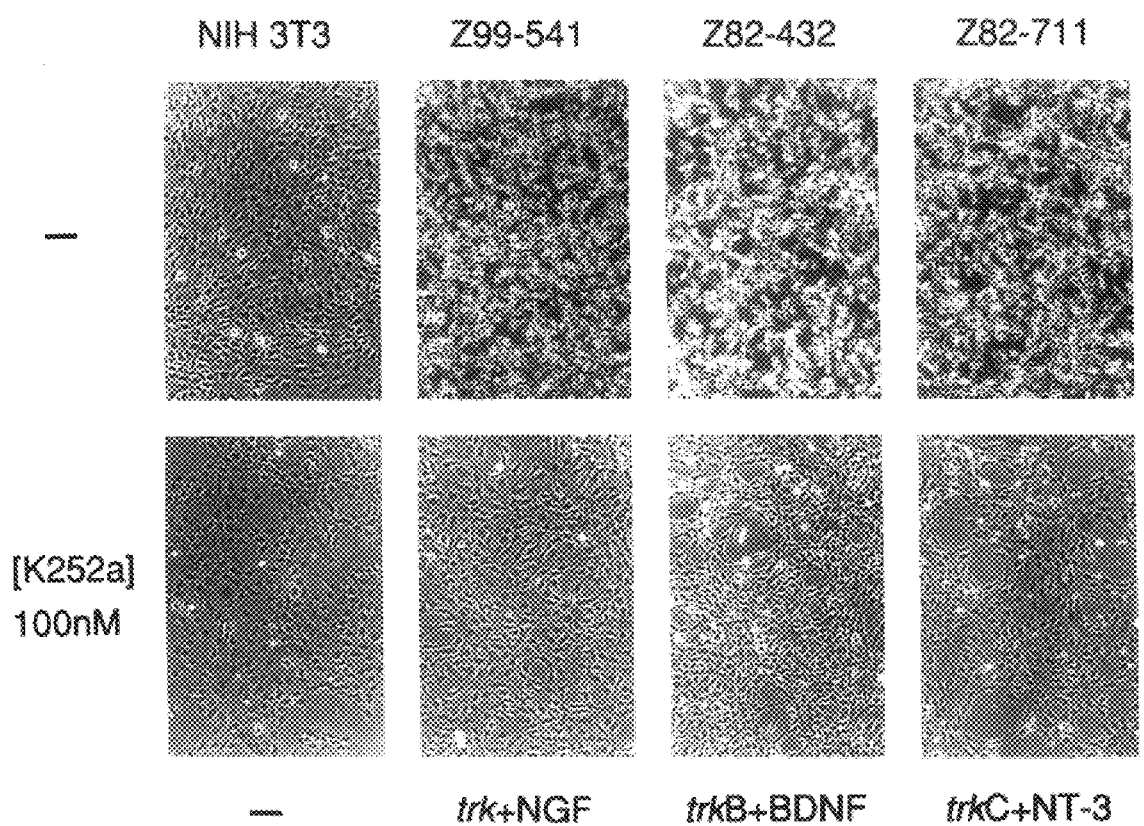

FIG. 5. K252a reverts the transformed phenotype of NIH3T3 cells transformed by co-expression of each of the members of the trk family of receptors with their respective ligands. Phase contrast micrographs (200×) of NIH3T3 cell lines transformed by co-transfection of plasmids encoding gp140$^{trk}$ and NGF (Z99–541 cells), gp145$^{trkB}$ and BDNF (Z82–432 cells), gp145$^{trkC}$ and NT-3 (Z82–711 cells). Cells were grown in the absence (−) or presence (+) of 100 nM K252a for 2 to 4 days.

Figure 6:
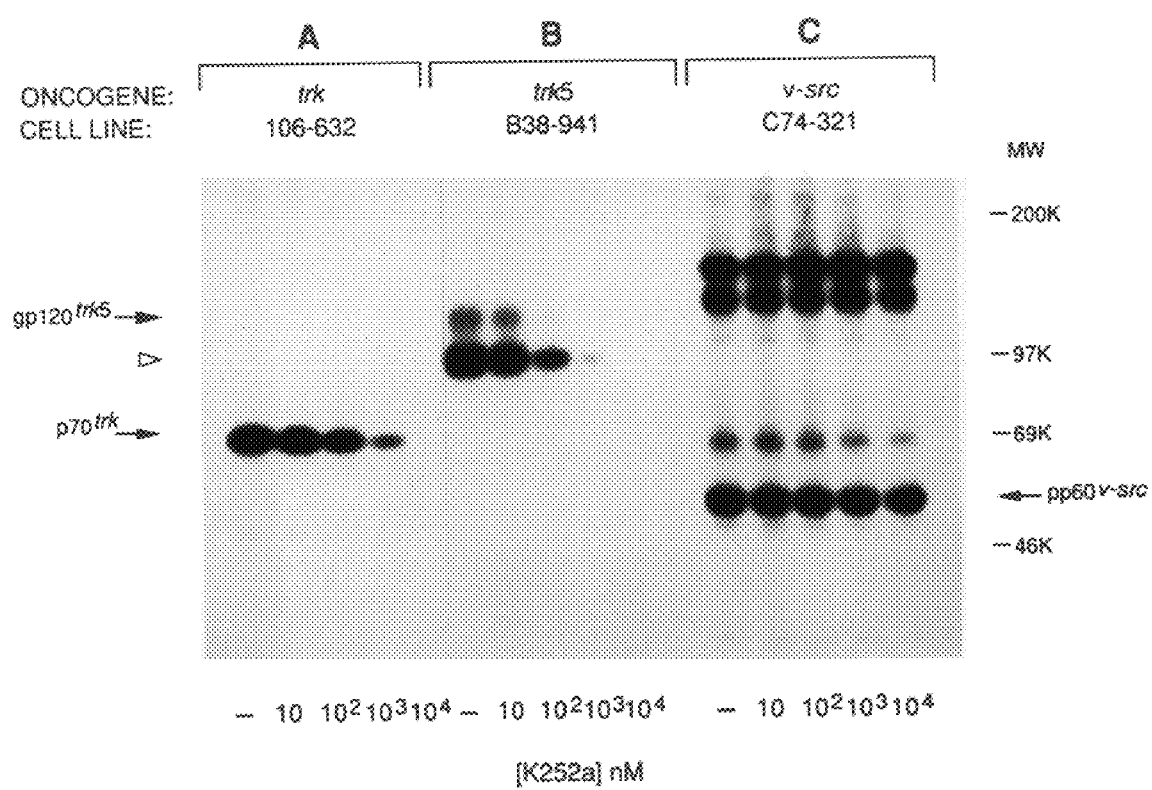

FIG. 6. Dose-dependent inhibition of the in vitro tyrosine protein kinase activity of trk oncoproteins by K252a. NIH3T3 cell lines transformed by (A) a human coloncarcinoma trk oncogene (106–632 cells), (B) the trk5 oncogene (B38–941 cells), and (C) v-src (C74–321 cells) were lysed in NP-40 lysis buffer and immunoprecipitated with (A,B) anti-gp140$^{trk}$ antiserum or (C) anti-pp60$^{v-src}$ monoclonal antibody 327 as described in Materials and Methods herein below. Immune complexes were incubated with the indicated concentrations of K252a for 5 minutes prior to the addition of [γ-$^{32}$P]-ATP. The in vitro kinase reactions were stopped by the addition of NP40 lysis buffer and analyzed by 8% SDS-PAGE. Gels were exposed to Kodak X-Omat film at −70° C. with the help of intensifying screens for 1 to 4 hours. The migration of p70$^{trk}$, gp120$^{trk5}$ and pp60$^{v-src}$ is indicated by arrows. The open arrow indicates the migration of a precursor of gp120$^{trk5}$. The higher molecular weight phosphorylated species shown in panel C are likely to represent co-precipitating pp60$^{v-src}$ substrates [(Reynolds, A. et al., Mol. Cell. Biol. 9, 3951–3958, (1989)]. Co-electrophoresed molecular weight markers are those described in the legend to FIG. 2.

Figure 7:
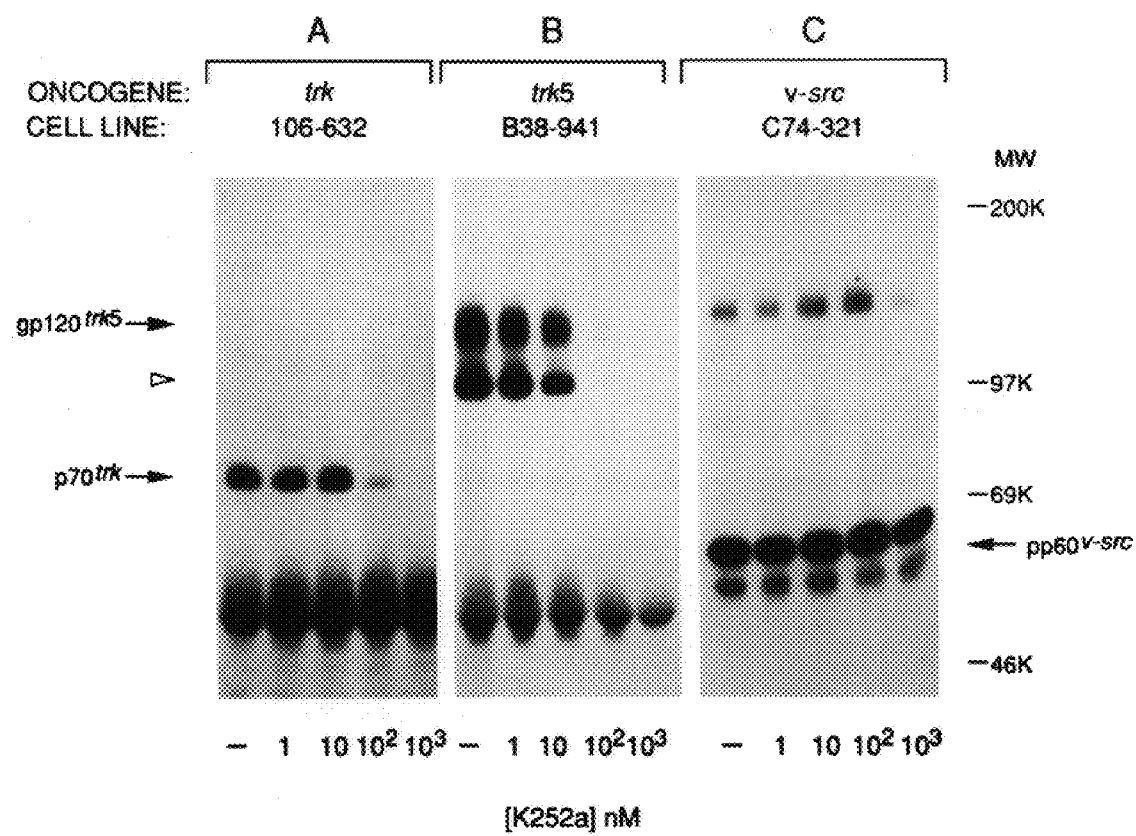

FIG. 7. Dose-dependent inhibition of in vivo tyrosine phosphorylation of trk oncoproteins by K252a. NIH3T3 cell lines transformed by (A) a human coloncarcinoma trk oncogene (106–632 cells), (B) the trk5 oncogene (B38–941 cells), and (C) v-src (C74–321 cells) were incubated for 18 hours in the presence of the indicated concentrations of K252a prior to lysis in PTYR buffer. Cell lysates were immunoprecipitated with (A,B) anti-gp140$^{trk}$ antiserum or (C) anti-pp60$^{v-src}$ monoclonal antibody 327 and fractionated by 8% SDS-PAGE. Samples were transferred to nitrocellulose filters and blotted with (A,B) anti-phosphotyrosine monlclonal antibody 4G10 or (C) polyclonal phosphotyrosine antiserum. Filters were incubated with [$^{125}$I]-protein A and exposed to Kodak X-Omat film at −70° C. with the help of intensifying screens for 6 hours. The migration of p70$^{trk}$, gp120$^{trk5}$ and pp60$^{v-src}$ is indicated by arrows. Co-electrophoresed molecular weight markers are those described in the legend to FIG. 2.

Figure 8:
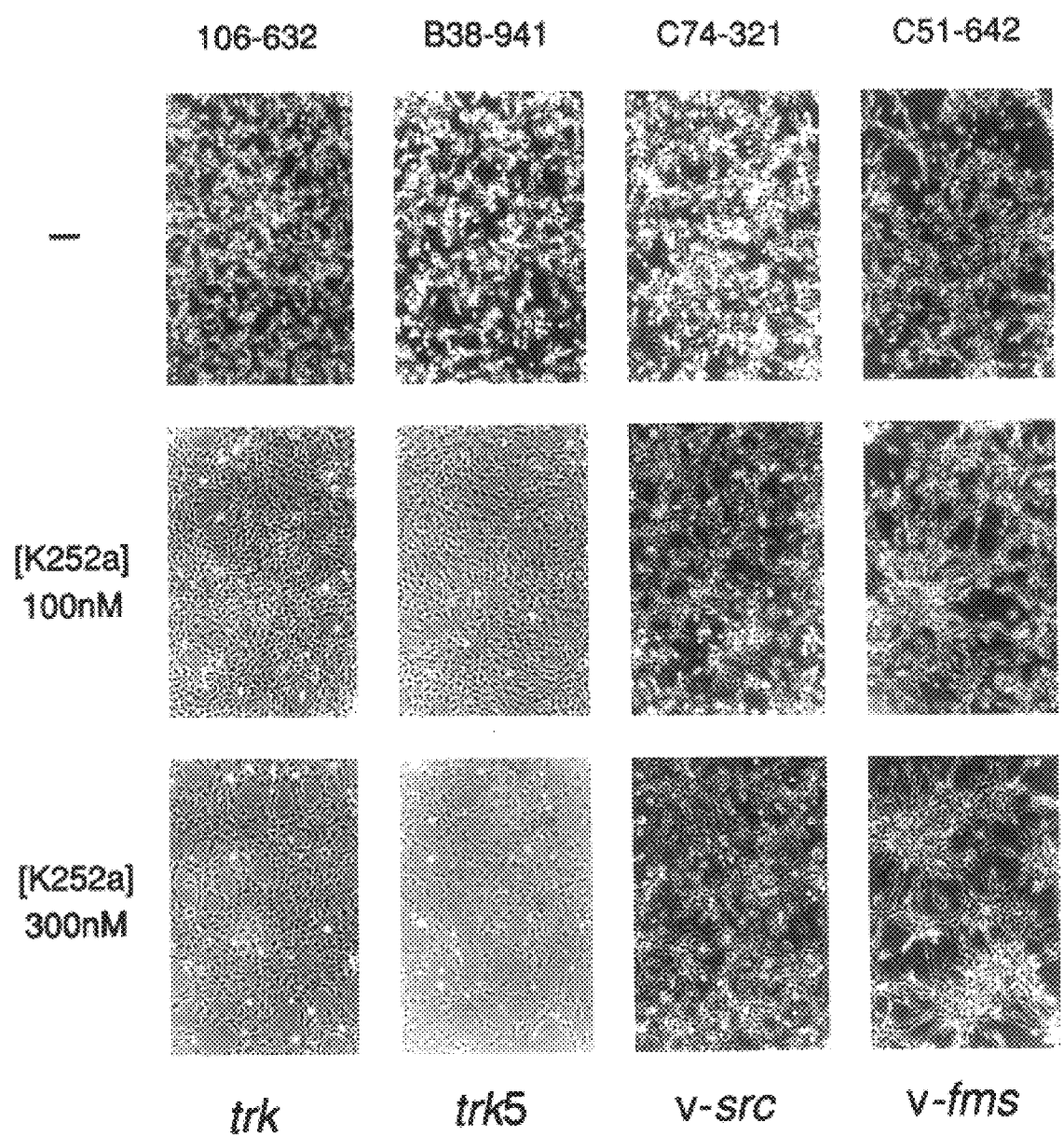

FIG. 8. K252a selectively reverts morphologic transformation induced by trk oncogenes. Phase contrast micrographs (200×) of NIH3T3 cells transformed by trk (106–632), trk5 (B38–941), v-src (C74–321) and v-fms (C51–642) oncogenes were grown for 2 to 4 days in the absence (−) or presence (+) of the indicated concentrations of K252a.

DETAILED DESCRIPTION OF THE INVENTION

The methods of the present invention can be used in the treatment of various cancers which are caused in whole or in part by oncogene encoded proteins which exhibit tyrosine protein kinase activity. Such oncogenes include any oncogene derived from the trk family or proto-oncogenes as well as other related tyrosine protein kinase oncogenes.

In particular, the methods of the present invention can be used to treat cancers which are caused by trk oncogene proteins containing a tyrosine protein kinase activity region; these are proteins encoded by trk oncogenes. trk oncogenes are derived from trk proto-oncogenes; trk proto-oncogenes encode trk family receptors. Included among the trk family receptors are trk, [See, Martin-Zanca, D. et al., Mol. Cell. Biol. 9, 24–33 (1989)], trk B [See, Klein, R. et al., EMBO J. 8, 3701–3709 (1989)] and trk C [See, Lamballe, F. et al., Cell 66, 967–979 (1991)] receptors.

Any tyrosine protein kinase inhibitor capable of inhibiting the protein kinase responsible for the particular cancer being treated may be used in accordance with the present invention. Suitable tyrosine protein kinase inhibitors include those of the formula

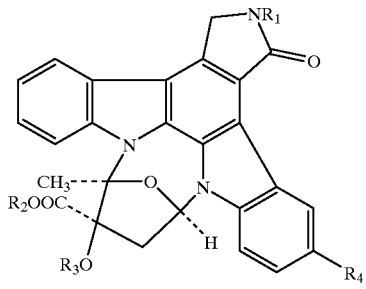

wherein $R_1$ is hydrogen or methyl, $R_2$ is hydrogen, methyl or n-hexyl, $R_3$ is hydrogen or methyl and $R_4$ is hydrogen or —OCH$_2$CH$_2$CH$_3$. Many of these compounds are commercially available from Kamiya Biomedical Company, Thousand Oaks, Calif. 91359. Particularly preferred is the compound wherein $R_1$, $R_3$ and $R_4$ are hydrogen and $R_2$ is methyl with the chemical name (8R*,9S*,11S*)-(-)-9-hydroxy-9-methoxycarbonyl-8-methyl-2,3,9,10-tetrahydro-8,11-epoxy-1H,8H,11H-2,7b,11a-triazadibenzo(a,g) cycloocta(c,d,e)triinden-1-one, and which is described in Biochem. Biophys. Res. Commun. 142, 436–440 (1987).

In carrying out the methods of the present invention, the tyrosine protein kinase inhibitor may be administered to various mammalian species, such as monkeys, dogs, cats, rats, humans, etc., in need of such treatment.

The tyrosine protein kinase inhibitor may be administered systemically, such as orally or parenterally, or the protein kinase inhibitor can be administered locally, for example, by topical administration.

The tyrosine protein kinase inhibitor may be incorporated in a conventional dosage form, such a tablet, capsule, elixir or injectable. The above dosage forms will also include the necessary carrier material, excipient, lubricant, buffer, antibacterial, bulking agent (such as mannitol), anti-oxidants (ascorbic acid or sodium bisulfite) or the like. Oral dosage forms are preferred, although parenteral forms are quite satisfactory as well.

With regard to such systems or local formulations, single or divided doses of from about 5 to about 2500 mg, preferably from about 10 to about 2000 mg/one to four times daily, may be administered in systemic dosage forms or locally as described above for a period sufficient to prevent, stabilize or cause regression of the cancer being treated.

The following example is further illustrated of the present invention, and examines the ability of the compound with the chemical name (8R*,9S*,11S*)-(-)-9-hydroxy-9-methoxycarbonyl-8-methyl-2-3-9-10-tetrahydro-8,11-epoxy-1H,8H,11H-2, 7b,11a-triazadibenzo(a,g)cycloocta(cde)trinden-1-one to inhibit the tyrosine protein kinase activity of the trk family of oncogenes and thereby reverse the transformation of neoplastic cells. This example is not intended to limit the scope of the present invention, and provides further understanding of the invention.

EXAMPLE

I. MATERIALS AND METHODS

A. Cell Lines.

NIH3T3 (Jainchill, J. L., et al. (1969). *J. Virol.*, 4, 549–553) and NIH3T3-derived cell lines were grown in DMEM containing 10% calf serum. They include: NIH3T3 cells expressing gp140$^{trk}$(E25-42 and E25-48; Klein, R., et al. (1991). *Cell*, 65, 189–197), gp145$^{trkB}$(Z52-17; Klein, R., et al. (1991). *Cell*, 66, 395–403), gp145$^{trkC}$(RA-31; Lamballe, F., et al. (1991). *Cell*, 66, 967–979), p70$^{trk}$ (106-632; Martin-Zanca, D., et al. (1986). *Nature*, 319, 743–748), pp60$^{v-src}$ (C74–321; Cuadrado, A., et al. (1990). *Cell Growth Diff.*, 1, 9–15), gp120$^{v-fms}$ (C51-642; Cuadrado, A., et al. (1990). *Cell Growth Diff.*, 1, 9–15), and gp120$^{trk5}$ (B38-941; Coulier, F., et al. (1990). *Mol. Cell. Biol.*, 10, 4202–4210). F19-91 cells, a NIH3T3-derived cell line that over-expresses the human EGF receptor, were obtained by transfecting NIH3T3 cells with pHERN3B, an expression plasmid encoding the human EGF receptor (provided by J. Schlessinger). NIH3T3-derived cell lines transformed by autocrine activation of the trk family of receptors were generated by co-transfecting NIH3T3 cells (Graham, F. L. & van der EB, A. J. (1973). *Virology* 53, 456–467) with the plasmids pDM69 (gp140$^{trk}$)+PLTRSNGF (NGF) (Z99–541 cells), pFKR44 (gp145$^{trkB}$)+pLL42 (BDNF) (Z82–432 cells) and pFL20 (gp145$^{trkC}$)+pLL43 (NT-3) (Z82–711 cells) [(Martin-Zanca, D., et al. (1989). *Mol. Cell. Biol.*, 9, 24–33; Cordon-Cardo, C., et al. (1991). *Cell*, 66, 173–183; Klein, R., et al. (1991). *Cell*, 66, 395–403; Lamballe, F., et al. (1991). *Cell*, 66, 967–979). Foci of transformed cells were picked with cloning cylinders and cloned by growth in semisolid agar as previously described (Oskam, R., et al. (1988). *Proc. Natl. Acad. Sci. USA*, 85, 2964–2968). Rat pheochromocytoma PC12 cells (Greene, L. A. & Tischler A. S., (1976). *Proc. Natl. Acad. Sci. USA*, 73, 2424–2428) were grown on collagen-coated dishes (Vitrogen) in DMEM containing 10% calf serum and 5% horse serum. To measure neurite outgrowth, PC12 cells were plated on 35 mm dishes at a density of 5×10$^4$ cells per plate. 24 hours after plating, factors were added at a concentration of 50 mg/ml in the absence or presence of K252a. The percentage of neurite outgrowth was scored as the percentage of cells showing neurites whose total length was at least twice the diameter of the cell body.

B. K252a, Factors and Antisera.

K252a was obtained from Kamiya Biomedical Company (Thousand Oaks, Calif.), dissolved in DMSO and stored in the dark at -20° C. Murine EGF, acidic and basic FGFs, 2.5 S NGF and human AB PDGF were purchased from Upstate Biotechnology Inc. (New York). BDNF and NT-3 were purified to about 95% homogeneity from supernatants of Sf9 insect cells infected with recombinant baculoviruses pAcS27 (BDNF) and pAcS28 (NT-3) as previously described (Cordon-Cardo, C., et al. (1991). *Cell*, 66, 173–183). Antisera included a rabbit antiserum (43-4) raised against a peptide corresponding to the carboxyl terminus of the gp140$^{trk}$ receptor (Martin-Zanca, D., et al. (1989). *Mol. Cell. Biol.*, 9, 24–33), a rabbit polyclonal antiserum (anti-PR 4, a gift of S. Courtneidge) against PDGF receptor (Kypta, R. M., et al. (1990). *Cell*, 62, 481–492), anti-human EGF receptor monoclonal antibody (Upstate Biotechnology Inc.), anti-pp60$^{v-src}$ monoclonal antibody 327 (Oncogene Sciences), anti-phosphotyrosine monoclonal antibody 4G10 (Upstate Biotechnology Inc.) and affinity purified rabbit anti-mouse immunoglobulins (Dako). A polyclonal phosphotyrosine antisera was prepared by immunization of rabbits with a poly-phosphotyrosine-glycine-alanine immunogen as described in Kamps, M. P. & Sefton, B. M. (1988). *Oncogene*, 2, 305–315.

C. Western Blot Analysis.

NIH3T3-derived cell lines were made quiescent by culturing them in DMEM containing 0.5% calf serum for 48 hours prior to growth factor stimulation. PC12 cells were not quiesced. After factor treatment, cells were rinsed in cold PBS containing 0.1 mM sodium orthovanadate before lysis in P-TYR lysis buffer (50 mM Hepes, pH 7.5; 1% Triton X-100; 50 mM NaCl; 50 mM NaF; 10 mM sodium pyrophosphate; 5mM EDTA; 0.5 mM sodium orthovanadate and 0.5 mM PMSF). Insoluble material was removed from the lysates by centrifugation at 12,000 rpm for 10 minutes. The clarified cell lysates were then incubated with the appropriate antisera and the resulting immunocomplexes collected by precipitation with protein A-Sepharose, washed four times with lysis buffer, fractionated by 8% SDS-PAGE and transferred to nitrocellulose filters as described by Harlow and Lane (1988), Antibodies: A Laboratory Manual (Cold Spring Harbor, N.Y.: Cold Spring Harbor Laboratory). The level of tyrosine phosphorylation of the receptors was determined by blotting with anti-phophotyrosine monoclonal antiobdy 4GlO and subsequent incubation with rabbit anti-mouse immunoglobulins and [$^{125}$I]-protein A (Dupont NEN) as described (Cordon-Cardo, C., et al. (1991). *Cell*, 66, 173–183). Western blot analysis of pp60$^{v-src}$ phosphorylation was performed as described above, except that the nitrocellulose filter was probed with a polyclonal phosphotyrosine antiserum.

D. In vitro Tyrosine Protein Kinase Assays.

Cells were rinsed with cold PBS containing 0.1 mM sodium orthovanadate and lysed in NP-40 lysis buffer (20 mM Tris-Cl pH 7.5; 150 mM NaCl; 1% aprotinin; 0.5 mM sodium orthovanadate; 2.5 mM EDTA; 10 mM NaF). The lysates were clarified and immunoprecipitated with the corresponding antisera as described above. The immune complexes were washed four times with NP-40 lysis buffer and once with 20 mM Hepes, pH 7.2 containing 50 mM NaCl and 1% aprotinin and resuspended in 47 µl of 20 mM Hepes, pH 7.2 containing 50 mM NaCl and 1% aprotinin and resuspended in 47 µl of 20 mM Hepes, pH 7.2 containing 10 mM $MnCl_2$. Samples were incubated at 30° C. for 5 minutes in the presence of the indicated concentrations of K252a. The kinase reactions were started by the addition of 10 µCi of [$\gamma$-$^{32}$P]-ATP (6000 Ci/mmol; Dupont NEN) and 4 µM ATP. The reactions were continued for 10 minutes at 30° C. and terminated by the addition of 0.5 ml of NP-40 lysis buffer. Samples were washed twice with NP-40 buffer and fractionated by 8% SDS-PAGE. Electrophoresed gels were washed with 1 N NaOH at 55° C. for 2 hours before autoradiography.

II. RESULTS

Figure 1:
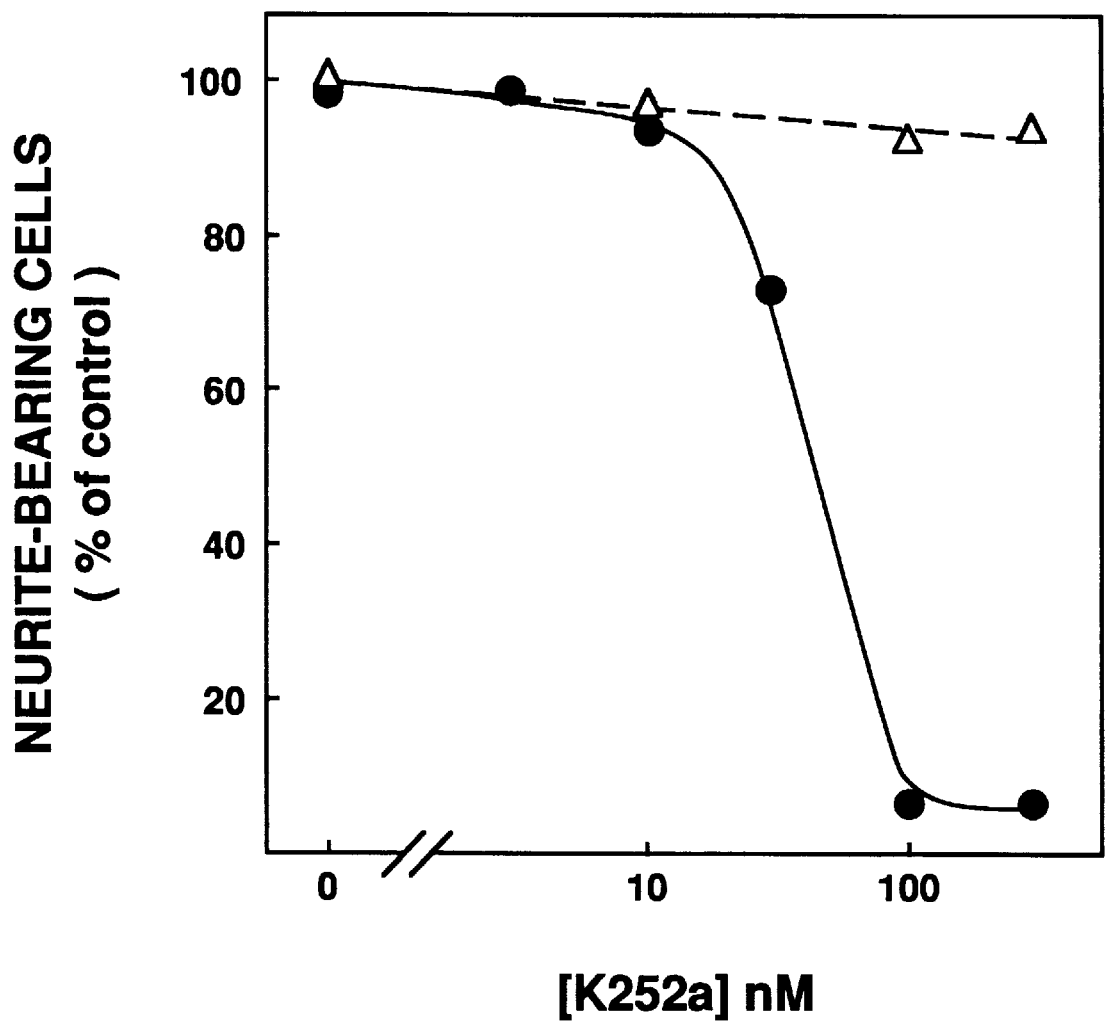

A. Differential Effect of K252a on Neuronal Differentiation of PC12 Cells Induced by NGF and FGFs Addition of neurotrophic factors such as NGF and FGF to PC12 cells induces their neuronal differentiation, a process characterized by the appearance of long neuritic outgrowths (Greene, L. A., & Tischler, A. S. (1982). In *Anvances in Cellular Neurobiology* (S. Federoff and L. Hertz, eds.), pp. 373–414, Academic Press, New York). In agreement with previous observations (Koizumi, S., et al. (1988). *J. Neurosci.*, 8, 715–721), the protein kinase inhibitor K252a efficiently blocked this differentiation process when induced by NGF. As indicated in FIG. 1, K252a blocked the appearance of neuritic processes in PC12 cells exposed to NGF with an $IC_{50}$ of about 40 nM. However, K252a had no detectable effect on the induction of neurite formation by another neurotrophic factor such as FGF, even at concentrations as high as 300 nM (FIG. 1). Interestingly, submicromolar concentrations of K252a did not have a significant inhibitory effect on the proliferation of PC12 cells (data not shown).

B. K252a Inhibits the Ligand-dependent Activation of the gp140$^{trk}$ NGF Receptor but not of other Tyrosine Kinase Growth Factor Receptors These results suggest that K242a blocks a specific component of the NGF-activated signal transduction pathway, most likely a protein kinase. Therefore, it was investigated whether K252a might block NGF-induced PC12 differentiation by inhibiting the tyrosine kinase activity of the NGF receptor, gp140$^{trk}$. For this purpose, serum-starved PC12 cells were incubated with 100 ng/ml of NGF in the absence or presence of 100 nM K252a. Cell extracts were immunoprecipitated with antibodies elicited against the carboxy terminal domain of gp140$^{trk}$, fractionated by SDS-PAGE and blotted with anti-phosphotyrosine antibodies. As shown in FIG. 2A, K252a completely abolished NGF-induced phosphorylation of gp140$^{trk}$ on tyrosine residues. Incubation of NIH3T3 cells with 100 ng/ml of PDGF in the presence of 100 nM K252a had no effect on the phosphorylation on typrosine residues of the PDGF receptor (FIG. 2C). Similar results were obtained when F19–91 cells, a NIH3T3 cell line overexpressing the human EGF receptor, with 100 ng/ml of EGF, were stimulated (FIG. 2B). These observations indicate that K252a is an inhibitor of the gp140$^{trk}$ tyrosine kinase receptor.

Figure 3:
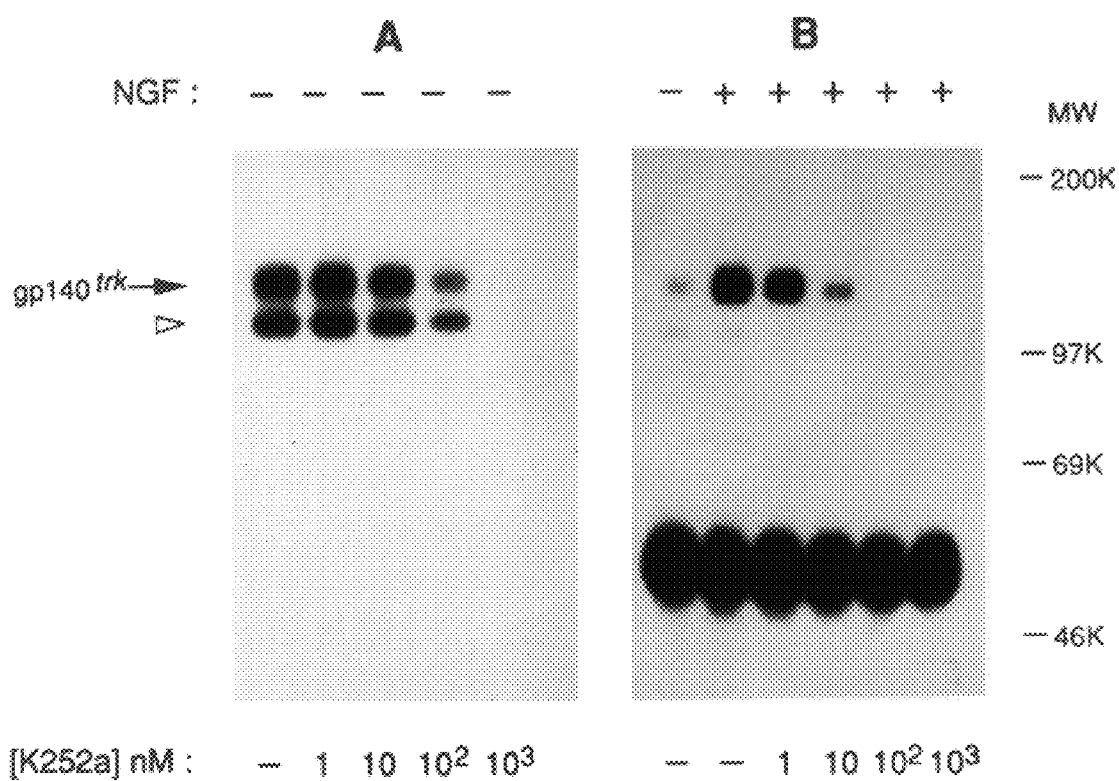
FIG. 3. Dose-dependent inhibition of the tyrosine protein kinase activity of gp140$^{trk}$ by K252a. (A) E25–48 cells were lysed in NP-40 lysis buffer and immunoprecipitated with anti-gp140$^{trk}$ antiserum as described in Material and Methods. The resulting immune complexes were incubated with the indicated concentrations of K252a for 5 minutes prior to the addition of [γ-$^{32}$P]-ATP. Reactions were stopped by the addition of NP40 lysis buffer and analyzed by 8% SDS-PAGE. Gels were exposed to Kodak X-Omat film at −70° C. with the help of intensifying screens for 18 hours. (B) Quiescent E25–42 cells were incubated for 18 hours in the presence of the indicated concentrations of K252a. Cells were incubated for an additional 10 minutes in the absence (−) or presence (+) of 100 ng/ml of NGF, lysed in P-TYR buffer and immunoprecipitated with anti-gp$^{trk}$ antiserum. The resulting immunoprecipitates were fractioned by 8%

Activation of tyrosine protein kinase receptors is thought to be mediated by a ligand-induced oligomerization step followed by autophosphorylation of their tyrosine residues (Ullrich, A. & Schiessinger, J. (1990). *Cell*, 61, 203–212). Thus, the above results are likely to be a consequence of the direct inhibitory effect of K252a on the catalytic activity of the gp140$^{trk}$ kinase. To formally demonstrate this hypothesis, the effect of K252a on the in vitro tyrosine kinase activity of immunoprecipitates containing the gp140$^{trk}$ receptor was examined. As shown in FIG. 3A, K252a efficiently inhibited the catalytic activity of gp140$^{trk}$ with an $IC_{50}$ of about 30 nM. In a parallel in vivo experiment, K252a inhibited the tyrosine phosphorylation of gp140$^{trk}$ with an $IC_{50}$ of about 3 nM (FIG. 3B). The lower inhibitory effect of K252a in vitro is likely to reflect the non-physiological conditions of this assay. However, the possibility that K252a may interact in vivo with structures outside the catalytic domain or with auxiliary proteins that affect the kinase activity of gp140$^{trk}$ cannot be excluded.

C. K252a is an Inhibitor of the trk Family of Neurotrophin Receptors

The gp140$^{trk}$ NGF receptor is a member of a small family of related tyrosine protein kinases which included gp145$^{trkB}$, a product of the trkB gene (Klein, R., et al. (1989). *EMBO J.*, 8, 3701–3709; Klein, R., et al. (1990). *Cell*, 61, 647–656; Middlemas, D. S., et al. (1991). *Mol. Cell. Biol.*, 11, 143–153), which mediates the biological activity of BDNF and to a lesser extent of NT-3 (Glass, D. J., et al. (1991). *Cell*, 66, 405–413); Klein, R., et al. (1991). *Cell*, 66, 395–403; Soppet, D., et al. (1991). *Cell*, 65, 895–903; Squinto, S. P., et al. (1991). *Cell* 65, 885–893), and gp145$^{trkC}$, a tyrosine protein kinase encoded by the trkC gene and a receptor specific for NT-3 (Lamballe, F., et al. (1991). *Cell*, 66, 967–979). It was investigated whether K252a was also an efficient inhibitor of the activation of these trk-related receptors by their cognate ligands. For this purpose, PC12 cells expressing gp140$^{trk}$ and NIH3T3 cell lines ectopically expressing gp140$^{trk}$ (E25–42 cells), gp145$^{trkB}$ (Z52–17 cells) and gp145$^{trkC}$ (RA-31 cells) were incubated with 100 ng/ml of NGF, BDNF and NT-3 respectively, in the absence or presence of 100 nM K252a. Cell extracts were immunoprecipitated with anti-gp140$^{trk}$ antibodies known to recognize each of the above receptors, fractionated by SDS-PAGE and blotted with antiphosphotyrosine antibodies. As shown in FIG. 4, 100 nM K252a completely abolished the phosphorylation on tyrosine residues of each of three ligand-activated receptors. Thus, K252a appears to be an inhibitor of the trk family of neurotrophin receptors.

D. K252a Inhibits the in vivo Mitogenic Activity of the trk Family of Neurotrophin Receptors It has been recently shown the co-expression of any of the known members of the trk family of receptors with their respective ligands in NIH3T3 cells elicits strong mitogenic signals (Cordon-Cardo, C., et al. (1991). *Cell*, 66, 73–183; Klein, R., et al. (1991). *Cell*, 66, 95–403; Lamballe, F., et al. (1991). *Cell*, 66, 967–979). This autocrine mitogenic activity results ultimately in the malignant transformation of these cells. These findings have made it possible to examine the in vivo acitvity of the trk receptor kinases independent of other components of the neurotrophin signal transduction pathway (e.g. P75$^{LNGFR}$) that may be required for their activity in either PC12 cells or more physiological environments such as neurons. NIH3T3 cells were co-transfected with expression plasmids encoding either gp140$^{trkB}$ (pDM69) and NGF (pLTRSNGF), gp145$^{trkB}$ (pFRK44) and BDNF (pLL42) or gp145$^{trkC}$(pFL20 and NT-3 (pLL43).

Transfected cells were then monitored for the appearance of foci of transformed cells either in the absence or presence of 100 nM K252a. In agreement with the previous studies, NIH3T3 cells were efficiently transformed by co-expression of each of the three members of the trk family of receptors with their respective ligands. However, this tranformation was completely abolished when transfected NIH3T3 cells were grown in the presence of 100 nM K252a (Table 1).

To determine whether K252a could revert the morphologic transformation induced by the autocrine activation of the trk family of receptors, NIH3T3 cell lines transformed by co-transfection of expression plasmids pDM69 and pLTRSNGF (Z99–541 cells), pFRK44 and pLL42 (Z82–432 cells), and pFL20 and pLL43 (Z82–711 cells) were generated. These cells were subsequently grown in the absence or presence of various concentrations (30 nM to 1 $\mu$M) of K252a, using untransfected NIH3T3 cells as controls. Micromolar concentrations of K252a were found to be considerably toxic, particularly to the untransfected NIH3T3 cells (data not shown). However, a significant effect on the growth properties of these cells at K252a concentrations of 300 nM or lower was not observed. As shown in FIG. 5, 100 nM K252a completely reverted the transformed phenotype of these NIH3T3-derived cell lines transformed by co-expression of the three members of the trk receptor family with their respective ligands. Lower K252a concentrations (30 nM) had a much more limited effect (data not shown). These results indicate that K252a is a potent inhibitor of the typrosine kinase activity of the trk family of receptors in vivo and that inhibition of this kinase activity blocks the mitogenic and transforming properties elicited by the trk receptors after autocrine stimulation by their respective ligands.

E. K252a Inhibits the Tyrosine Kinase Acitvity of trk Oncogenes

Genetic rearrangements in the human trk proto-oncogene locus have been implicated in the development of certain human cancers including colon and thyroid papillary carcinomas (Martin-Zanca, D., et al. (1986). *Nature*, 319, 743–748; Bongarzone, I., et al. (1989). *Oncogene*, 4, 1457–1462). Therefore, it was examined whether K252a might also be a selective inhibitor of these human oncogenes. Two classes of trk oncogenes were selected for these studies (Barbacid, M., et al. (1991). *BBA Reviews in Cancer*, in press). One class includes a cDNA clone of the original human colon carcinoma oncogene in which its entire ligand-binding domain has been replaced by non-muscle tropomyosin sequences. This trk oncogene encodes a 70,000 dalton cytoplasmic protein, $p70^{trk}$, that no longer resembles a transmembrane receptor (Martin-Zanca, D., et al. (1986). *Nature*, 319, 743–748). The second oncogene selected for this study was trk5, an oncogene generated during gene transfer by an in-frame deletion that resulted in the loss of 51 amino-acid residues in the extracellular domain of the trk proto-oncogene product (Oskam, R., et al. (1988). *Proc. Natl. Acad. Sci. USA*, 85, 2964–2968; Coulier, F., et al. (1990). *Mol. Cell. Biol.*, 10, 4202–4210). As a consequence, the trk5 oncogene encodes a 120,000 dalton glycoprotein, $gp120^{trk5}$, that retains the basic structural features of tyrosine protein kinase receptors (Oskam, R., et al. (1988). *Proc. Natl. Acad. Sci. USA*, 85, 2964–2968; Coulier, F., et al. (1990). *Mol. Cell. Biol.*, 10, 4202–4210).

As shown in FIG. 6, K252a inhibited the in vitro kinase activity of both of these trk oncogene products, $p70^{trk}$ and $gp120^{trk5}$, with $IC_{50}$s of 300 and 100 nM, respectively. In contrast, concentrations of K252a as high as 10 $\mu$M did not have any significant inhibitory effect on the catalytic activity of $pp60^{v-src}$, an unrelated tyrosine protein kinase (FIG. 6C). Similar results were obtained when the effect of K252a on the levels of tyrosine phosphorylation of the $p70^{trk}$ and $gp120^{trk5}$ oncoproteins present in NIH3T3 cell lines tranformed by the human trk (106–632 cells) and the in vitro-generated trk5 (B38–941 cells) oncogenes, respectively, was measured. As indicated above, the levels of tyrosine phosphorylation of these proteins is likely to reflect their in vivo autophosphorylation activity. As depicted in FIG. 7, K252a efficiently inhibited tyrosine phosphorylation of both these oncoproteins with $IC_{50}$s of about 50 nM ($p70^{trk}$) and 30 nM ($gp120^{trk5}$). In agreement with the results obtained in the in vitro kinase assay, K252a did not have any inhibitory effect on the levels of tyrosine phosphorylation of $pp60^{v-src}$ even at concentrations as high as 1 $\mu$M (FIG. 7C).

F. K252a Reverts the Transformed Phenotype Induced by trk Oncogenes

The above results suggested that K252a may also be able to revert the transformed phenotype of NIH3T3 cells transformed by these trk oncogenes. As shown in FIG. 8, treatment of trk-transformed 106–632 cells or trk5-transformed B38–941 cells for as little as 36 hours in the presence of 100 nM K252a completely reverted their transformed phenotype. Up to a 3-fold higher concentrations of K252a had no effect on the morphology of NIH3T3 cell lines transformed by several other tyrosine protein kinase oncogenes including v-src (C74–321 cells), and v-fms (C51–642 cells), another oncogene derived from a tyrosine protein kinase receptor (FIG. 8). Treatment of these v-src and v-fms NIH3T3 transformed cells with increasing concentrations of K252a revealed the appearance of toxic effect (at about 1 $\mu$M) without any signs of morphologic reversion (data not shown). These results establish that K252a is an inhibitor of the transforming properties of trk oncogenes regardless of the nature of their activating mutation(s).

III. DISCUSSION

Tyrosine protein phosphorylation is one of the principal mechanisms by which cells transduce extracellular signals into proliferating and/or differentiating responses (Cantley, L. C., et al. (1991). *Cell*, 64, 281–302). Many growth factors including insulin, IGF-I, EGF, PDGFS, FGFS, CSF-1, SF, HGF and the NGF family of neurotrophins, mediate their biological functions through tyrosine protein kinase receptors. In addition, an increasing number of cytoplasmic tyrosine protein kinases such as the members of the Src family, c-Abl and c-Fes/Fps are known to participate in signal transduction (Cantley, L. C., et al. (1991). *Cell*, 64, 281–302). The variety of physiological functions mediated by these tyrosine protein kinases has made them an attractive target for the development of specific inhibitors. To date, several tyrosine protein kinase inhibitors have been isolated such as erbstatin, genistein, herbimycin A, lavendustin A and the trphostins. Unfortunately, these inhibitors show little selectivity for the various tyrosine protein kinases, thus making them unsuitable for therapeutic use.

Submicromolar concentrations of K252a, a known inhibitor of serine/threonine kinases (Kase, H., et al. (1986). *J. Antibiot*, 39, 1059–1065; Kase, H., et al. (1987). *Biochem. Biophys. Res. Commun.*, 142, 436–440), completely inhibit the in vitro tyrosine protein kinase activity of the NGF receptor, $gp140^{trk}$. More importantly, K252a inhibits NGF-mediated autophosphorylation of $gp140^{trk}$ receptors in vivo with an $IC_{50}$ of 3 nM. Similar results were obtained when we used the related $gp145^{trkB}$ and $gp145^{trkC}$ tyrosine protein kinases which serve as receptors for the NGF-related neurotrophins BDNF and NT-3, respectively (Glass, D. J., et al.

(1991) *Cell*, 66, 405–413; Klein, R., et al. (1991). *Cell*, 66, 395–403; Lamaballe, F., et al. (1991). *Cell*, 66, 967–979; Soppet, D., et al. (1991). *Cell*, 65, 895–903; Squinto, S. P., et al. (1991). *Cell*, 65, 885–893). In contrast, K252a had no effect on the autophosphorylation activity of the EGF and PDGF receptors when activated by their cognate ligands. These observations indicate that K252a is a powerful inhibitor of the tyrosine protein kinase activity of the trk family of neurotrophin receptors.

Autocrine stimulation of each of the trk receptors by their respective cognate ligands results in the morphologic transformation of NIH3T3 cells. Concentrations of K252a as low as 100 nM completely blocked this tranforming activity and reverted the transformed phenotype of NIH3T3 cells co-expressing the trk receptors and their corresponding ligands. Interestingly, concentrations of K252a as high as 300 nM have no significant effect on the proliferation rate of these NIH3T3-derived cells nor elicit any detectable toxic effects. Therefore, K252a appears to be a more efficient inhibitor of the trk family of receptors than of serine/threonine kinases such as protein kinase C, whose activity is likely to be required for the proper metabolic functioning of these cells.

The trk proto-oncogene can acquire transforming properties by a variety of genetic alterations (Barbacid, M., et al. (1991). *BBA Reviews in Cancer*, in press). Most of these mutation results in the generation of trk oncogenes whose products no longer exhibit the structural characteristics of cell surface receptors. In human tumors, trk oncogenes have their extracellular sequences replaced by unrelated genes such as non-muscle tropomyosin (Martin-Zanca, D., et al. (1986). *Nature*, 319, 743–748) and tpr (Greco et al., submitted for publication). In addition, trk sequences can recombine in vitro leading to the frequent generation of trk oncogenes (Kozma, S. C., et al. (1988), *EMBO J.*, 7, 147–154; Oskam, R., et al. (1988). *Proc. Natl. Acad. Sci. USA*, 85, 2964–2968). Some of these in vitro-generated trk oncogenes resemble those found in human tumors in that their extracellular sequences are replaced by foreign genes. Others are activated by point mutations or small in-frame deletions in their extracellular sequences which do not result in the loss of their basic cell surface receptor structures (Coulier, F., et al. (1990). *Mol. Cell. Biol.*, 10, 4202–4210). As illustrated in this study, K252a is an efficient inhibitor of the tyrosine protein kinase activity of trk oncogenes regardless of whether they encode cytoplasmic or cell surface molecules. K252a appears, however, to be about one order of magnitude more efficient in inhibiting the tyrosine kinase activity of the normal trk receptor than those of its oncogenic alleles. The more limited inhibitory activity of K252a on trk oncogenes is likely to be a consequence of structural alterations in their catalytic domains caused by those mutations responsible for their oncogenic activation.

In spite of the lower $IC_{50}$ with which K252a inhibits the kinase activity of trk oncogenes, concentrations of 100 nM of this inhibitor efficiently reverted the transformed phenotype of NIH3T3 cells expressing either the human colon carcinoma trk transforming gene or the in vitro-generated trk5 oncogene. In contrast, concentrations of K252a as high as 1 $\mu$M had no effect on the transformed phenotype of NIH3T3 cells containing the tyrosine protein kinase oncogenes v-src and v-fms.

K252a is a member of a group of natural (staurosporine, K252b) and synthetic (KT5720, KT5823, KT5926) alkaloids which are thought to exert their biological activity by competing with the binding of ATP to the kinase catalytic domain (Kase, H., et al. (1986). *J. Antibiot.*, 39, 1059–1065; Kase, H., et al. (1987). *Biochem. Biophys. Res. Commun.*, 142, 436–440). The inhibitory effect of K252a on the catalytic activity of normal and oncogenic trk kinases should help to establish the structural basis for the rational design of tyrosine protein kinase inhibitors.

TABLE 1

K252a Inhibits the Transformation of NIH3T3 Cells by Co-transfection of Expression Plasmids Encoding the trk Family of Receptors and their Ligands.

| CO-TRANSFECTED DNAs[a] | | | Trans forming |
|---|---|---|---|
| PLASMID (Receptor) | PLASMID (Neurotrophin) | K252a 100 nM | Activity (Foci per $10^5$ cells) |
| — | — | — | 0 |
| pDM69(gp140[trk]) | pLTRSNGF (NGF) | — | >1000 |
| pDM69(gp140[trk]) | pLTRSNGF (NGF) | + | 0 |
| pFRK44(gp145[trkB]) | pLL42 (BDNF) | — | >1000 |
| pFRK44(gp145[trkB]) | pLL42 (BDNF) | + | 0 |
| pFL20(gp145[trkC]) | pLL43 (NT-3) | — | >1000 |
| pFL20(gp145[trkC]) | pLL43 (NT-3) | + | 0 |

[a]100 ng of receptor DNA and 1 $\mu$g of neurotrophin DNA were used for each transfection [Graham, F. L. and van der Eb, A. J., Virology 53, 456–467 (1973)].

What is claimed is:

1. A method for preventing, stabilizing or causing regression of cancer induced by a trk oncogene protein, which comprises adminstering to a mammalian species in need thereof a therapeutically effective amount of a tyrosine protein kinase inhibitor wherein the tyrosine protein kinase inhibitor is selected from compounds of the formula

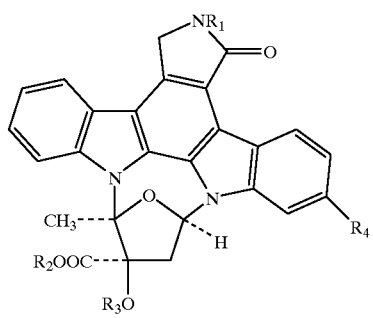

wherein $R_1$ is hydrogen or methyl, $R_2$ is hydrogen, methyl or n-hexyl, $R_3$ is hydrogen or methyl and $R_4$ is hydrogen or —OCH$_2$CH$_2$CH$_3$.

2. The method of claim 1 wherein said tyrosine protein kinase inhibitor is (8R*, 9S*, 11S*)-(−)-9-hydroxy-9-methoxycarbonyl-8-methyl-2,3,9,10-tetrahydro-8, 11-epoxy-(1H, 8H, 11H) 2, 7b, 11a-triazadibenzo(a, g)cycloocta(c, d, e)triinden-1-one.

3. The method according to claim 1 wherein the mammalian species is a human.

* * * * *